United States Patent [19]

Worrell et al.

[11] 4,192,656
[45] Mar. 11, 1980

[54] METHOD AND APPARATUS FOR HALTING THE ADVANCEMENT OF ACCIDENTAL ETHYLENE DECOMPOSITION IN A GAS PIPELINE

[75] Inventors: G. Richard Worrell, Media, Pa.; Frank F. McKay, Jr., Baytown, Tex.

[73] Assignee: Atlantic Richfield Company, Los Angeles, Calif.

[21] Appl. No.: 860,791

[22] Filed: Dec. 15, 1977

[51] Int. Cl.² .................. F17D 1/02; F17D 1/04
[52] U.S. Cl. ................................ 48/192; 137/334; 165/1; 165/DIG. 14
[58] Field of Search .............. 48/190, 191, 192; 138/38; 137/334, 338; 206/0.6; 220/88 R; 165/1, DIG. 14

[56] References Cited

U.S. PATENT DOCUMENTS

| | | | |
|---|---|---|---|
| 996,130 | 6/1911 | Pelton | 138/38 |
| 1,259,029 | 3/1918 | Lucke | 48/192 |
| 1,339,431 | 5/1920 | Backhause | 206/0.6 |
| 2,087,170 | 7/1937 | Stephenson | 48/192 |
| 2,730,438 | 1/1956 | Kemp | 48/190 |
| 2,772,537 | 12/1956 | Lisciani | 48/192 |
| 3,071,452 | 1/1963 | Braconier et al. | 48/190 |
| 3,763,262 | 10/1973 | Sato et al. | 165/1 |
| 3,830,063 | 8/1974 | Morgan | 165/DIG. 14 |

FOREIGN PATENT DOCUMENTS 764167 of 1934 France .................. 48/192

Primary Examiner—S. Leon Bashore
Assistant Examiner—Peter F. Kratz
Attorney, Agent, or Firm—John R. Ewbank

[57] ABSTRACT

In a system in which compressed ethylene is scheduled to flow through pipes, and in which there is danger of decomposition of ethylene and danger of the spreading of a reaction boundary of the exothermic decomposition reaction, a method and means are provided for quenching the advancement of the decomposition. Ethylene is directed from large diameter pipes into an array of spaced apart small diameter tubes which are not overheated when subjected to the combination of head and tail boundaries of the advancing plug of decomposition products. Such overheating of the tubes by the leading and trailing flames can be prevented by cooling the exterior of the tubes with a fluid normally maintained at about ambient temperature, thereby cooling the compressed ethylene sufficiently to quench the decomposition reaction. The cooling fluid is desirably an aqueous system adapted to be converted to steam under severe conditions. A significant depth of liquid is normally maintained above the upper strata of tubes in the reaction boundary suppressors so that the total cooling capacity of the liquid, before evaporation exposes an upper strata of tubes, is significantly greater than in the dormant liquid of a heat exchanger of conventional design. This system of quenching reactions has applicability to facilities featuring the flow of gases other than ethylene. The system comprising the piping for the compressed gas includes such reaction boundary suppressors at locations appropriate for protecting critical zones of compressed gas from the hazard of the advancement of an undesired accidental reaction.

6 Claims, 3 Drawing Figures

METHOD AND APPARATUS FOR HALTING THE ADVANCEMENT OF ACCIDENTAL ETHYLENE DECOMPOSITION IN A GAS PIPELINE

BACKGROUND OF INVENTION

1. FIELD OF INVENTION

This invention relates to compressed ethylene and systems involving the piping of compressed ethylene along relatively great distances. In its broader aspects, it relates to reaction boundary suppressors in facilities in which a reaction boundary such as a flame front of an undesired reaction (initiated by an accident) has a propensity to migrate through a gas pipeline. The similar minimizing of the spreading of flames through a gas pipeline system is sometimes discussed in relation to the strategy of placement of flame arrestors.

PRIOR ART

It has long been known that a saturated hydrocarbon gas, such as ethane, propane, or methane, could be compressed and transmitted through pipelines without significant problems other than the hazard of combustion. By maintaining acetylene at about atmospheric pressure and quite pure, acetylene can be handled safely. At an early date, it was learned that acetylene was quite hazardous when compressed by reason of its propensity to undergo a decomposition. The flame speed for such decomposition is greater than the speed of sound, thus classifying the reaction as a detonation instead of deflagration. The early discovery of the violence of the detonation of compressed acetylene resulted in municipal ordinances prohibiting systems using compressed acetylene.

Compressed ethylene is neither as safe as compressed ethane nor as dangerous as compressed acetylene. It has been known that a decomposition reaction could advance throughout a great length of a pipe containing compressed ethylene. The temperature of the spontaneously advancing decomposition reaction is hot enough to cause blistering of paint on the external surface of a pipe in which compressed ethylene decomposes to a mixture comprising soot, carbon, minor amounts of hydrogen, minor amounts of miscellaneous hydrocarbon, and a molar amount of methane approximately equal to the initial ethylene. The speed of the flame is quite low, eliminating the detonation hazard but permitting explosions of vessels unable to withstand the pressures built up by the decomposition reaction. The build-up of pressure is attributable primarily to the increased temperature of the gas mixture, instead of the conventional volume increasing reaction. Because piping for compressed ethylene is built with an adequate safety feature, it is conceivable that the decomposition reaction boundary might move through a pipe for a very considerable distance without any explosion and even without any rupture of the pipe.

The amount of cooling necessary for quenching an accidental reaction is affected by many factors, including flame speed, exothermicity of the reaction, magnitude of gas compression, pipe diameter, single or multiple flames, and related factors. Heretofore most flame arrestors have had a cooling capacity which is only a small fraction of the cooling capacity necessary to quench the forward and trailing reaction boundaries for the decomposition of ethylene at 100 atmospheres in a pipeline of about 30 cm diameter. Because accidents sometimes involve hazards which had not been predicted, there has been a long standing demand for flame arrestors having an adequate safety margin as regards cooling capacity sufficient to quench a reaction.

In a pipe in which compressed ethylene is flowing and in which a localized surge of heat initiates decomposition reaction boundaries, such boundaries can initially move in two opposite directions or in as many directions as the piping system permits. In the typical single pipe in which the decomposition reaction boundaries start moving initially in two opposite directions and in which the ethylene is flowing in one of those two directions, the pipe is heated by each of the two reaction boundaries advancing in the same direction as the flowing ethylene. Whether the boundaries are identified as leading and trailing boundaries or as head and tail boundaries, the second arriving boundary is more difficultly quenched because of the residual heat from the first arriving boundary.

The speed of each reaction boundary is only a small fraction of the normal speed of the flow of the ethylene. The temperature of a particular zone of the pipe is increased because of the passage of each of the two flame fronts through such zone, usually within minutes of each other. Moreover, the methane gas and suspended soot in the methane zone between the two reaction boundaries is hot enough to warm the pipe but undergoes cooling. The total heat capacity of a plug-zone of decomposition products (conveniently called a methane zone) and the two reaction boundaries is far greater than the heat capacities of advancing segments of hot gases for which some flame arrestors have been designed. Some flame arrestors have been designed for flame speeds much higher than the remarkably slow speed of advancement of the ethylene cracking reaction boundary, which is sometimes a few (i.e. from 3 to 20) cm per minute and rarely if ever faster than 4000 cm per minute. It is the combination of the potentially low speed of advancement of the reaction boundary and the remarkably large heat capacity of the elongated methane zone which imposes unique restraints upon quenching the ethylene decomposition reaction.

The exothermic decomposition of the ethylene corresponds to the general equation $$C_2H_4 \rightarrow CH_4 + C$$

Because the reaction mixture is heated by the exothermic reaction, and such heat tends to expand the gas, one easily overlooks the fact that the equation involves no change in volume of the gas. The soot which is formed generally contains only about 1% hydrogen. Although methane is the principal gaseous product, minor amounts of many hydrocarbon materials and hydrogen can form under the unusual conditions leading to the thermal cracking (i.e. decomposition) of ethylene.

Chemical engineers have been dealing with compressed ethylene for more than 50 years, and have long been aware of the accidental decomposition hazard. The range of incipient decomposition conditions, above which decomposition cannot readily be prevented, and below which decomposition is initiated with greater difficulty, has been investigated. The boundary of the decomposition reaction can advance more readily within such incipient conditions as the pressure is increased, as the temperature is increased, and as the hot tube diameter is increased. Systems utilizing compressed ethylene ordinarily have featured process conditions intended by the engineers to significantly decrease the possibility of the accidental decomposition of compressed ethylene. Thus compressors for ethylene are generally operated so that the peak temperature of the compressed gas is kept below the danger point.

Notwithstanding the processing of large quantities of compressed ethylene during the past century, the number of serious catastrophies attributable to the unintended decomposition of ethylene reported in the safety literature has been relatively small. Hence ethylene decomposition accidents have been treated as nuisance problems. Some petroleum technologists are essentially unaware of the ethylene decomposition hazard.

Ethylene is relatively inexpensive compared to acetylene and/or some other gaseous reactants which might be lost by flame migration. There has not been a willingness to invest in unusual safety equipment for ethylene in the way that there has been for chemicals known to be more costly or more hazardous. There has been a continuing demand for a simple system for coping with the hazards pertinent to the decomposition of ethylene, while still preserving the low investment cost and low maintenance cost essential for handling of compressed ethylene.

In its broader aspects, various gas pipeline systems have employed flame arrestors and related devices to quench the advancement of a reaction boundary (generally called a flame front) beyond established limits. The complexity and large capital investment required for prior art systems has created a long standing and continuing demand for an appropriate means and method for quenching an undesired reaction advancing through a pipeline system.

SUMMARY OF INVENTION

In accordance with the present invention, a system in which ethylene flows through pipes is protected for halting the advancement of a boundary of the decomposition of ethylene by providing reaction boundary suppressors at appropriate locations in the system, thereby decreasing the possibility of accidental advancing into a zone of critical danger. Each reaction boundary suppressor comprises an array of spaced apart tubes through which portions of the gas stream flow to cool and quench such gas stream. A fluid normally maintained at about ambient temperature serves to cool the exterior walls of said tubes. An aqueous system (e.g. aqueous ethylene glycol containing corrosion inhibitors, etc.) and normally lying dormant, and designed to get warmer (even to volatilize glycol vapor and steam) when cooling a methane zone and its boundaries is preferably employed. Such pool of aqueous coolant must be deep enough to provide a significant depth of liquid above the top strata of tubes. When a flame front (or reaction boundary) advances to heat the liquid, and possibly volatilize some of the liquid, the amount of liquid above the uppermost row of tubes is sufficient that the liquid level will not fall below such top tubes before the plurality of flame fronts have been quenched. Each reaction boundary suppressor also includes means for connecting the suppressor to an inlet pipe and to an exit pipe, together with entry plenum means and exit plenum means for directing the gas from the entry pipe, through the entry plenum, through the array of tubes, through the exit plenum, and into the exit pipe. Such gas flow resembles the flow of gas through a water cooled heat exchanger of the tube and shell type. However, because the gas is circulating, but the aqueous liquid is normally a dormant pool in a relatively deep vat in a reaction boundary suppressor, there are numerous structural differences from a conventional tube and shell heat exchanger. A steam vapor outlet permits the liquid to be volatilized from a suppressor. The topmost tubes of a suppressor are at a significant depth below the normal liquid level. The suppressor tubes are spaced apart at distances promoting prompt quenching of the reaction boundary instead of at distances favoring economical heat transfer from a circulating liquid. Conventional tube and shell heat exchangers rely upon pumping systems to circulate the liquid. In a reaction boundary suppressor, the pool of liquid is normally dormant and quiescent for months. Even when a flame front enters a reaction boundary suppressor, the liquid circulation is merely that attributable to temperature differences without the turbulence and rapid turnover of a pump driven circulation system.

DESCRIPTION OF DRAWINGS

In the accompanying drawings.

ILLUSTRATIVE EMBODIMENTS

Figure 1:
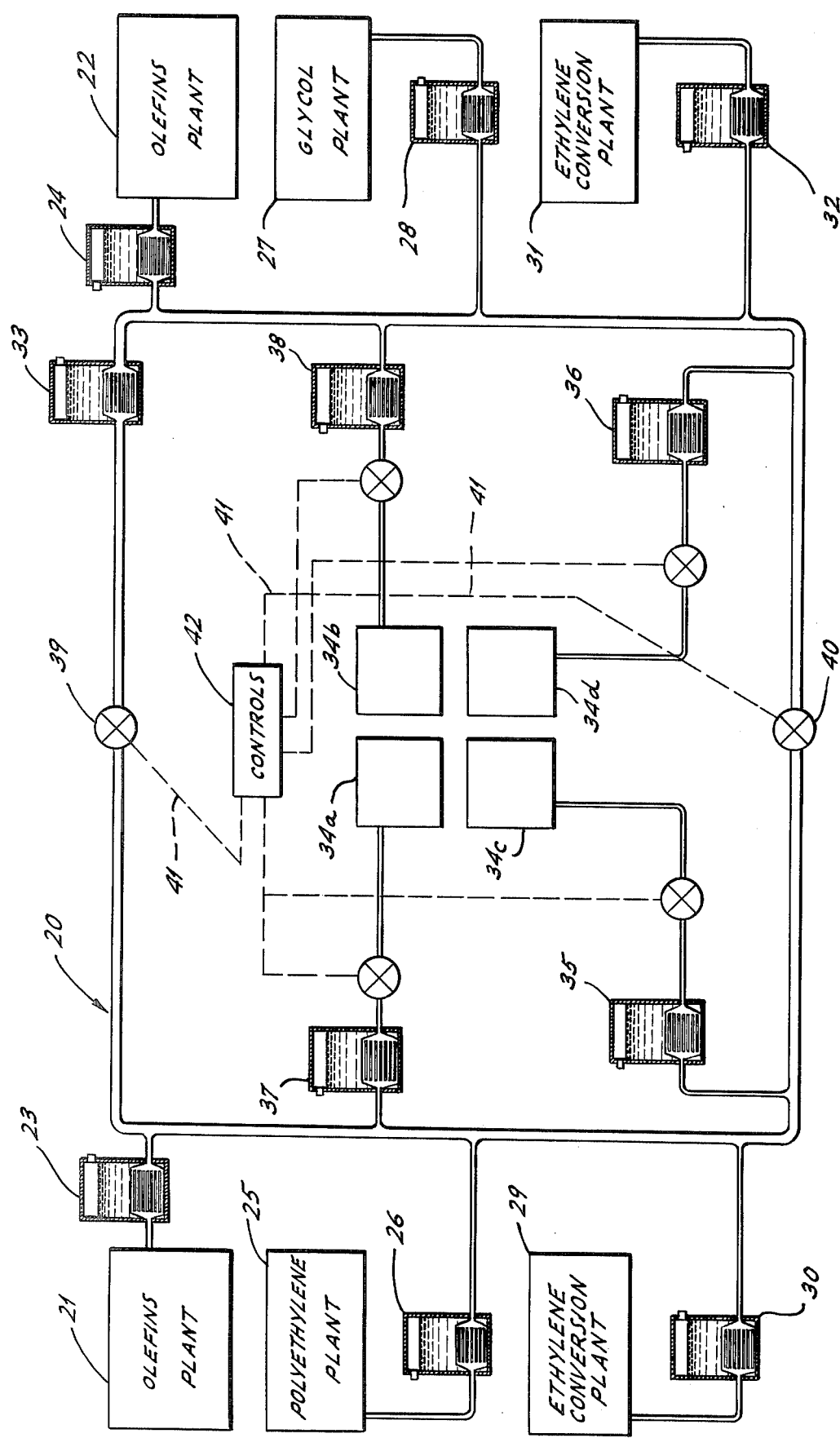
FIG. 1 is a schematic flow sheet of a gas line piping system featuring reaction boundary suppressors to quench any advancing boundary of exothermic reaction at zones ahead of where the gas stream might enter any critical zone.

As shown in FIG. 1, a gas pipeline system 20 can be a loop of 30 cm. steel pipe permitting the flow of compressed ethylene at about 100 atmospheres to circulate and/or flow from plants in which the ethylene is produced to plants in which the ethylene is consumed. The schematic showing of FIG. 1 indicates that the ethylene is produced in two olefins plants 21 and 22. Such ethylene is directed from plants 21 and 22 into the gas pipeline system 20 through reaction boundary suppressors 23 and 24, so that the hazard of any accidental decomposition of ethylene does not advance from the pipeline system 20 into either olefins plant.

Some of the ethylene is employed in the production of polyethylene in a polyethylene plant 25. Particular attention is directed to the fact that a reaction boundary suppressor 26 is interposed between the ethylene pipeline system 20 and the polyethylene plant 25. Similarly, a glycol plant 27 is protected by a reaction boundary suppressor 28. Additional plants for the conversion of ethylene, shown as 29 and 31, are similarly protected by reaction boundary suppressors 30, 32. FIG. 1 symbolizes one pattern of flexibility in production, transportation, storage and consumption of ethylene by showing a plurality of ethylene conversion plants associated with a plurality of ethylene sources and an appropriate ethylene storage facility through the gas pipeline system 20.

A reaction boundary supporessor 33 in pipeline system 20 symbolizes the potentiality of protecting a portion of a pipeline from the effects of an advancing boundary of an exothermic cracking reaction. Any accidental decomposition reaction merely destroying a plug of ethylene in the pipeline can be treated as a loss of ethylene which is not a relatively costly matter. The explosion and rupture of a pipeline is the more serious hazard which the safety engineers seek to prevent, while tolerating the migration of a decomposition reaction as long as it is strictly within what is merely a pipeline. However, it is very important that the compressed ethylene maintained in four standby storage systems 34 a,b,c,d be protected from the accidental decomposition reaction. The quantity of ethylene in any of such storage systems is large enough to merit protection. Accordingly, each of the storage systems 34 a,b,c, and d is protected by a reaction boundary suppressor 35, 36, 37 and 38 respectively. When valves 39 and 40 are open, the piping system 20 partakes of the nature of a closed loop. Communication lines 41 provide sensing signals and actuating signals to controls 42 intended to improve the functioning of storage system 34.

Figure 2:
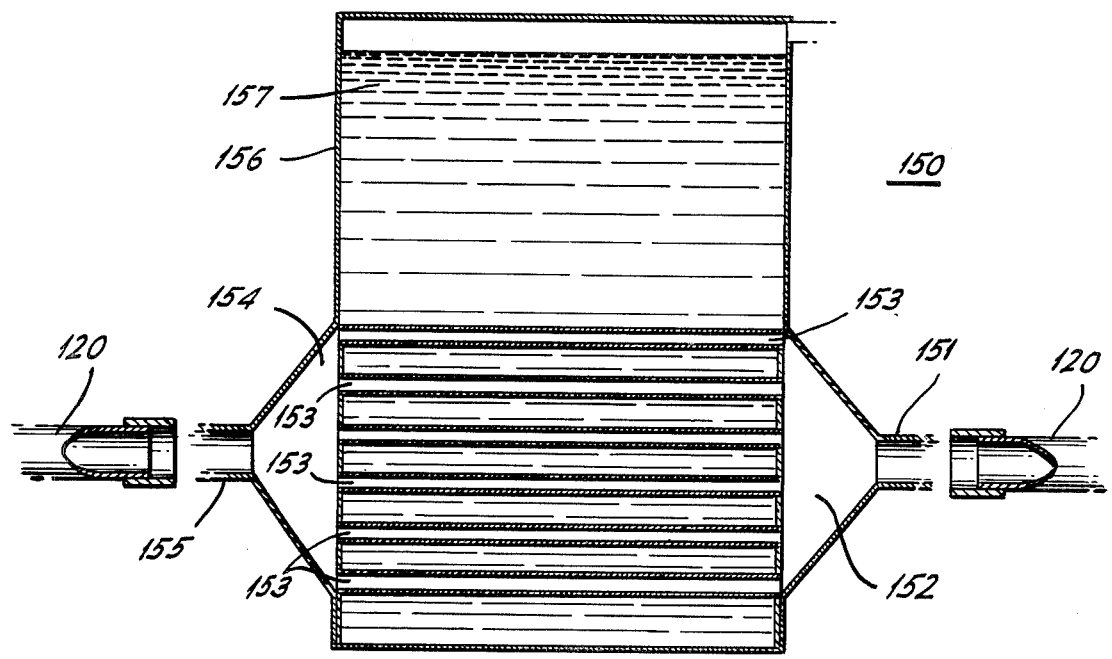
FIG. 2 is a schematic showing of a tube and shell-type of reaction boundary suppressor effective for the quenching of the advancing boundary of the exothermic cracking reaction of compressed ethylene.

As shown in FIG. 2, a reaction boundary suppressor 150 comprises a pipe 151 adapted to connect with an appropriate portion of a pipeline system 120 for the compressed ethylene. The gas entering through pipe 151 is distributed in a plenum 152 to a sufficient number of small tubes 153 that the cross sectional area of the plurality of tubes 153 is equivalent to a reasonable percentage (e.g. 10% to 300%) of the cross sectional area of 151. Each of tubes 153 is spaced from adjacent tubes sufficiently to permit the flow of an aqueous system therebetween in accordance with good engineering practice for promoting efficient heat exchange with the dormant cooling capacity of the pool of liquid. At the other end of the reaction boundary suppressor, there is an exit plenum 154 and exit pipe 155 which directs the effluent from the heat exchanger back into pipeline system 120. A shell 156 defines a vat 157 containing an aqueous system (e.g. water containing ethylene glycol, corrosion inhibitors, etc.) adapted to cool the tubes 153 immersed therein.

Safety studies relating to the speed of travel of the boundary of a reaction in a pipeline are generally discussed in terms of flame speeds. The accidental reaction most often investigated is that of a combustible gas with oxygen. The visible flame from such combustion can be followed with motion pictures when the flame is traveling in transparent tubing. The reaction of methane and oxygen leads to a flame speed described in some literature as about 39 centimeters per second, which is similar to the flame speed for combustion of ethyl acetate. The combustion of the acetylene is significantly faster, having a flame speed of 163 centimeters per second. Hydrogen burns with a flame speed of 306 centimeters per second. An estimated speed of reaction of a hydrocarbon with bromine, chlorine, nitric oxide or other reactant can be calculated using the flame speed for combustion with oxygen and thermodynamic data for the reaction.

The decomposition of ethylene is quite remarkable by reason of the measurement of flame speeds which vary significantly depending upon variables such as pressure, temperature, tube diameter, turbulence, and the like. Speeds as low as about 0.1 centimeter per second have been reported for the cracking of ethylene, but its peak speed is not so clearly established, but is apparently less than 67 cm per second. The extent to which a pipe can be overheated as well as the ease of environmental cooling to a quenching temperature are affected by the flame speed of the reaction. If the gas stream is advancing in one direction, and the decomposition is advancing in the opposite direction at the substantially identical speed, a static boundary can exist which tends to heat the pipeline wall to the temperature of the decomposition reaction. Such purely static boundaries are sufficiently rare that they are of more theoretical than practical interest. It is important to recognize that the quenching of the advancing ethylene decomposition reaction boundary when it is migrating (the resultant of the gas stream flow and the flame speed) at even a few centimeters per second is much easier than when such boundary migration approaches static conditions by migrating, for example, at less than about 3 cm. per second In the broader aspects of the invention, the use of a reaction front suppressor as a flame arrestor has applicability to substantially any gaseous mixture which might be accidentally reacting in a pipeline system. The important need is that of permitting a sufficient cooling of the gaseous mixture to assure the cooling of the reaction mixture below the point at which the reaction can be propagated. If the reaction boundary suppressor consists of tubes having about 1 or 2 centimeters inside diameter and a length of about 3 meters, and if the number of tubes is such that the cross sectional area of the tubes is about one-half the cross sectional area of the main pipeline, then the water cooling by the reaction boundary suppressor can quench most of the flames which might accidentally occur in gas pipeline systems. The total heat capacity of the hot zone which must be quenched in most gas pipelines in only a small fraction of the heat capacity of the plug of methane and two decomposition boundaries which can develop in a compressed ethylene pipeline system. Only rarely does the pipeline encounter the double boundary difficulty involving on exothermic reaction at each end of a moving plug of hot zone as occurs in the decomposition of compressed ethylene. For most gas pipeline systems, the quenching of the initial flame front is sufficient to improve the safe conditions within the pipeline system.

Particular attention is directed to the fact that the normal level of the aqueous liquid is far above the topmost tube through which the gas stream flows. Normally, the gas stream is at the same ambient temperature as the liquid in the reaction boundary suppressor. If an accidental reaction starts in the pipeline, and migrates to the inlet of the reaction boundary suppressor, then the liquid is heated as the reaction boundary starts moving through the small tubes of the reaction boundary suppressor. Under favorable conditions, the reaction can be quenched before the liquid is heated to its boiling point. The reserve cooling capacity of a reaction boundary suppressor is attributable in part to the cooling by evaporation of steam (and the vapor of the antifreeze agent such as ethylene glycol) from the top of the liquid. As the liquid boils away and as the liquid level is lowered, the tubes continue to be cooled to such boiling liquid temperature which is below about 150° C., thus being cool enough to quench the reaction. Only after the liquid has been evaporated until the top layer of tubes is exposed is there loss of the potentiality of the liquid cooling.

The depth of the liquid above the topmost tube is desirably somewhat greater than the depth of the liquid below such topmost tube, assuming that the cross-sectional area of the liquid is generally the same at all depths. Under some conditions, it may be appropriate to employ a reservoir above the tubes which is either smaller or larger in cross sectional area than the zone in which the tubes are immersed in the liquid. The liquid in the vat can be designated as a dormant pool of cooling liquid.

A reaction boundary suppressor can rely upon air cooling for achieving the desired cooling of the gas stream flowing through the array of small tubes. The spacing of the tubes from each other in the array of tubes is generally great enough to assure convection flow of the air from the tubes to the environment. It is essential that sufficient cooling surface be provided to assure the cooling of the gas stream to a temperature below the reaction temperature during the flow through the length of the array of tubes. A plurality of supports is generally employed between the two ends of the air cooled reaction boundary suppressor.

Figure 3:
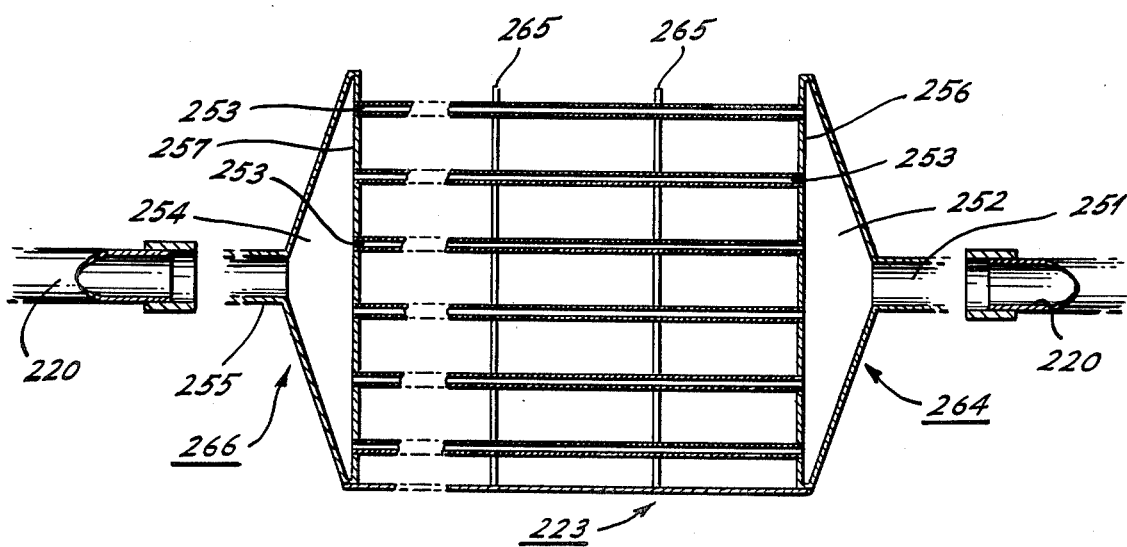
FIG. 3 is a schematic showing of an alternative type of reaction boundary suppressor.

As shown in FIG. 3 a reaction boundary suppressor 223 includes an entry pipe 251 which can be associatable with a pipeline system 220. Entry means comprising such entry pipe 251 permits the gas to flow from the pipeline system 220 into a plenum 252 and thence into a sufficient number of small tubes 253 that the cross sectional area of the array of tubes 253 is equivalent to a reasonable percentage (for example, 10% to 300% or typically 50%) of the cross sectional area of entry pipe 251. A wall 256 has openings to which the ends of the tubes are welded so that the exterior of the tubes 253 are exposed to the atmosphere. A plurality of supports 265 help to maintain the correct spacing of the array of atmosphericly exposed tubes 253 between entry means 264 and exit means 266. A plenum 254 allows the gas to flow from the array of tubes 253 into exit pipe 255 which is associatable with pipeline system 220. A wall 257 (analogous to wall 256) helps to confine the gas flowing through plenum 254. The tubes may have a length such as 7 meters adequate to assure appropriate cooling of the gas stream during passage through the length of the array of atmosphericly cooled tubes 253. Although reference is made to entry pipe 251 and exit pipe 255, it should be recognized that such terms relate to the direction of the gas flow in the pipeline and that the reaction boundary suppressor 223 is effective in quenching a reaction without regard to the direction of flow of the gas stream therethrough.

Each reaction boundary suppressor has a standby capacity for suddenly cooling a plug of hot gas which unexpectedly arrives at one end, so that the gas leaving the other end is assuredly cooled to a temperature so low that the undesired reaction is quenched. The heat from such accidental plug of hot gas is dissipated into the environment because of the extremely large dormant cooling capacity of the reaction boundary suppressor.

The reaction boundary suppressor of the present invention can be utilized as a flame arrestor in any of a considerable number of the situations in which flame arrestors have been used heretofore. A characteristic of the invention is providing a quantity of cooling of the gas stream that is significantly greater than the amount of cooling which has been typical of many previous flame arrestors. The present invention can be deemed to be pertinent to a system comprising pathways for the flow of gas which normally can flow safely, but which is susceptible to accidental participation in an exothermic. reaction capable of advancing in various directions from a point of origin, and features a system for halting the advancement of a reaction boundary of such exothermic reaction which consists of controlling the path of the gas flow so that, at appropriate zones of contemplated flow of the gas, the gas, instead of flowing through a conventional portion of a gas pipe line, is directed through an array of thin gas streams having effective cross sectional dimensions not greater than about 4 centimeters, and having a length greater than about a meter; and cooling said thin gas streams by heat exchanging said gas streams with a fluid normally maintained at about ambient temperature, whereby the gas immediately adjacent any advancing reaction boundary is cooled below reaction temperature in said thin gas streams, and whereby the gas completing the flow through said thin gas streams does not undergo the exothermic reaction because of the quenching thereof by said heat exchange with the cooling fluid.

To the extent that the present invention is deemed to be concerned with an apparatus as distinguished from a method, the subject matter can be clarified as an apparatus for halting the advancement of the reaction boundary of an exothermic reaction in a gas pipe line system in which a gas normally can flow safely, but which gas is susceptible to accidental participation in an exothermic reaction capable of advancing in at least one direction from a point of origin, said apparatus consisting of: an array of narrow tubes having a length of at least 1 meter and an internal diameter not greater than about 4 centimeters through which the gas stream is adapted to flow; structural means adapted to maintain the exterior of said array of narrow tubes in a fluid normally maintained at about ambient temperature, and adapted to cool the gas flowing within said array of tubes to a temperature below flame temperature, whereby in the event of the advancement of a reaction boundary into one end of the array of narrow tubes the reaction boundary is cooled and quenched to below reaction temperature before such reaction boundary can advance to the other end of such tubes; entry means directing gas flowing through an entry pipe associatable with a gas pipe line into said array of tubes; and exit means directing gas flowing through said array of tubes into an exit pipe associatable with a gas pipe line.

The present invention, whether as a system or apparatus, has particular applicability for controlling the migration of the reaction boundary of the decomposition reaction of compressed ethylene.

Various modifications of the invention are possible without departing from the scope of the appended claims.

The invention claimed is:

1. In a system for the pipeline flow of compressed ethylene along relatively great distances, wherein non-catalytic decomposition of ethylene to form carbon, miscellaneous products, and methane is an exothermic reaction which can advance from a point of origin in various directions, the method of halting the advancement of a reaction boundary of such decomposition reaction which consists of:

controlling the path of the compressed gaseous ethylene so that, at appropriate zones of contemplated flow of ethylene, the ethylene instead of flowing through a conventional portion of a gas pipeline, is directed through an array of narrow tubes having cross-sectional dimensions of not more than 4 centimeters and having a length greater than a meter, and cooling the ethylene in said plurality of narrow tubes by transferring heat from the ethylene to a liquid normally maintained below about 150° C., whereby the compressed ethylene flowing throughout the entire length of said narrow tubular stream is quenched to a temperature below the decomposition temperature of ethylene at such conditions.

2. In a system for the pipeline flow of compressed ethylene along relatively great distances, wherein non-catalytic decomposition of ethylene to form carbon, miscellaneous products, and methane is an exothermic reaction which can advance from a point of origin in various directions, the apparatus for halting the advancement of a reaction boundary of such decomposition reaction which consists of:

an array of narrow tubes having a length of at least 1 meter and an internal diameter of not greater than about 4 centimeters through which said compressed ethylene flows;

a shell defining a vat, said vat containing a pool of liquid normally maintained at about ambient temperature, the upper surface of the pool of liquid being exposed to the surroundings in such manner that vapor may evaporate from the upper surface of the liquid, said array of tubes being immersed significantly below the surface of said pool of liquid;

entry means directing gas flowing through an entry pipe connected to said gas pipe line into said plurality of tubes; and exit means directing gas flowing through said plurality of tubes into an exit pipe connected to said gas pipe line.

3. In a ethylene gas pipe line system comprising pathways for the flow of gas which normally can flow safely along relatively great distances in said pipeline system, but which is susceptible to accidental participation in an exothermic reaction capable of advancing in various directions from a point of origin, the apparatus for halting the advancement of a reaction boundary of such exothermic reaction which consists of:

an array of narrow tubes having a length of at least 1 meter and an internal diameter not greater than about 4 centimeters through which the gas stream is adapted to flow;

structural means for maintaining the exterior of said array of narrow tubes immersed significantly below the upper surface of a liquid normally maintained at about ambient temperature, and adapted to cool the gas flowing within said array of tubes to a temperature below about 150° C., whereby in the event of the advancement of a reaction boundary into one end of the array of narrow tubes the reaction boundary is cooled and quenched to below reaction temperature before such reaction boundary can advance to the other end of such tubes;

entry means directing gas flowing through an entry pipe connected to said gas pipeline into said array of tubes; and exit means directing gas flowing through said array of tubes into an exit pipe connected to said gas pipeline.

4. In a ethylene gas pipeline system comprising pathways for the flow of a gas which normally can flow safely along relatively long distances in said pipeline system, but which is susceptible to accidental participation in an exothermic reaction capable of advancing in various directions from a point of origin, the method of halting the advancement of the reaction boundary of such exothermic reaction in the gas pipeline system which consists of:

controlling the path of the gas flow so that, at appropriate zones of contemplated flow of the gas, the gas, instead of flowing through a conventional portion of a gas pipeline, is directed through an array of narrow tubes having cross sectional dimensions of not greater than about 4 centimeters, and having a length greater than about a meter, and cooling the gas in said narrow tubes by heat exchanging said gas with a liquid normally maintained at about ambient temperature, whereby the gas flowing through said narrow tubes does not undergo the exothermic reaction because of the quenching thereof by said heat exchange with the cooling liquid.

5. The apparatus of claim 3 in which the entry means and exit means are sufficiently equivalent that the potential flow of reaction boundary may be through the array of tubes in either direction, whereby what is utilized as the entry means and exit means is controlled by the direction of the flow of reaction boundary in the pipeline.

6. The apparatus of claim 3 in which a vaporizable aqueous system serves as the liquid maintained normally at about ambient temperature.

* * * * *